(12) United States Patent
Chen et al.

(10) Patent No.: US 7,598,039 B2
(45) Date of Patent: Oct. 6, 2009

(54) TREATMENT OF INSULIN RESISTANCE

(75) Inventors: Chih-Cheng Chen, Taipei (TW);
Shyh-Jer Huang, Taipei County (TW);
Yi-Wen Lin, Taichung County (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/668,952

(22) Filed: Jan. 30, 2007

(65) Prior Publication Data

US 2008/0181881 A1  Jul. 31, 2008

(51) Int. Cl.
*C12Q 1/68* (2006.01)

(52) U.S. Cl. .......................................... 435/6

(58) Field of Classification Search ........................ 435/6
See application file for complete search history.

(56) References Cited

U.S. PATENT DOCUMENTS

| 5,847,008 | A | 12/1998 | Doebber et al. | |
|---|---|---|---|---|
| 6,090,839 | A | 7/2000 | Adams et al. | |
| 6,287,859 | B1 | 9/2001 | DeWeille et al. | |
| 6,635,432 | B1 | 10/2003 | Welsh et al. | |
| 6,727,260 | B2 | 4/2004 | Varming et al. | |
| 2006/0234242 | A1* | 10/2006 | Cheatham et al. | 435/6 |
| 2007/0281986 | A1* | 12/2007 | Collier et al. | 514/403 |

OTHER PUBLICATIONS

Waldemann et al. (JBC, 272: 20975-20978, 1997).*
Kaiser Science, 317, 2007, 580.*
Chao et al (The Mount Sinai J of Medicine, 2004, 305-312).*
Scherer et al. (Nat. Biotechnol., 2003, 21(12), pp. 1457-1465.*
Mahato et al. (Expert Opinion on Drug Delivery, Jan. 2005, vol. 2, No. 1, pp. 3-28).*
An et al., "Genome-wide Linkage Scans for the Fasting Glucose, Insulin, and Insulin Resistance in the National Heart, Lung, and Blood Institute Family Blood Pressure Program," *Diabetes*, 54:909-914 (2005).
Chen et al., "A Role for ASIC3 in the Modulation of High-Intensity Pain Stimuli," *PNAS*, 99(13):8992-8997 (2002).
Diochot er al., "A New Sea Anemone Peptide, APETx2, Inhibits ASI3, a Major Acid-Sensitive Channel in Sensory Nuerons," *The EMBO Journal*, 23:1516-1525 (2004).
Voilley et al., "Nonsteriod Anti-Inflammatory Drugs Inhibit Both the Activity and the Inflammation-Induced Expression of Acid-Sensing Ion Channels in Nociceptors," *The Journal of Neuroscience*, 21(20):8026-8033 (2001).
Voilley, N., "Acid-Sensing Ion Channels (ASICs): New Targets for the Analgesic Effects of Non-Steroid Anti-Inflammatory Drugs (NSAIDs)," *Curr. Drug Targets Inflamm. Allergy*, 3(1):71-79 (2004).
Yuan et al., "Reversal of Obersity-and-Diet-Induced Insulin Resistance with Salicylates or Targeted Dsruption of *Ikkβ*" *Science*, 239:1673-1677 (2001).

* cited by examiner

*Primary Examiner*—Brian Whiteman
(74) *Attorney, Agent, or Firm*—Occhiuti Rohlicek & Tsao LLP

(57) ABSTRACT

Disclosed are a method of for treating insulin resistance and a method identifying a compound for treating insulin resistance.

10 Claims, No Drawings

SEQUENCE LISTING

```
<160> NUMBER OF SEQ ID NOS: 59

<210> SEQ ID NO 1
<211> LENGTH: 531
<212> TYPE: PRT
<213> ORGANISM: Homo sapiens

<400> SEQUENCE: 1

Met Lys Pro Thr Ser Gly Pro Glu Glu Ala Arg Arg Pro Ala Ser Asp
 1               5                  10                  15

Ile Arg Val Phe Ala Ser Asn Cys Ser Met His Gly Leu Gly His Val
            20                  25                  30

Phe Gly Pro Gly Ser Leu Ser Leu Arg Arg Gly Met Trp Ala Ala Ala
        35                  40                  45

Val Val Leu Ser Val Ala Thr Phe Leu Tyr Gln Val Ala Glu Arg Val
    50                  55                  60

Arg Tyr Tyr Arg Glu Phe His His Gln Thr Ala Leu Asp Glu Arg Glu
65                  70                  75                  80

Ser His Arg Leu Ile Phe Pro Ala Val Thr Leu Cys Asn Ile Asn Pro
                85                  90                  95
```

-continued

```
Leu Arg Arg Ser Arg Leu Thr Pro Asn Asp Leu His Trp Ala Gly Ser
            100                 105                 110
Ala Leu Leu Gly Leu Asp Pro Ala Glu His Ala Ala Phe Leu Arg Ala
        115                 120                 125
Leu Gly Arg Pro Pro Ala Pro Pro Gly Phe Met Pro Ser Pro Thr Phe
    130                 135                 140
Asp Met Ala Gln Leu Tyr Ala Arg Ala Gly His Ser Leu Asp Asp Met
145                 150                 155                 160
Leu Leu Asp Cys Arg Phe Arg Gly Gln Pro Cys Gly Pro Glu Asn Phe
                165                 170                 175
Thr Thr Ile Phe Thr Arg Met Gly Lys Cys Tyr Thr Phe Asn Ser Gly
            180                 185                 190
Ala Asp Gly Ala Glu Leu Leu Thr Thr Thr Arg Gly Gly Met Gly Asn
        195                 200                 205
Gly Leu Asp Ile Met Leu Asp Val Gln Gln Glu Glu Tyr Leu Pro Val
    210                 215                 220
Trp Arg Asp Asn Glu Glu Thr Pro Phe Glu Val Gly Ile Arg Val Gln
225                 230                 235                 240
Ile His Ser Gln Glu Glu Pro Pro Ile Ile Asp Gln Leu Gly Leu Gly
                245                 250                 255
Val Ser Pro Gly Tyr Gln Thr Phe Val Ser Cys Gln Gln Gln Leu
            260                 265                 270
Ser Phe Leu Pro Pro Pro Trp Gly Asp Cys Ser Ser Ala Ser Leu Asn
        275                 280                 285
Pro Asn Tyr Glu Pro Glu Pro Ser Asp Pro Leu Gly Ser Pro Ser Pro
    290                 295                 300
Ser Pro Ser Pro Pro Tyr Thr Leu Met Gly Cys Arg Leu Ala Cys Glu
305                 310                 315                 320
Thr Arg Tyr Val Ala Arg Lys Cys Gly Cys Arg Met Val Tyr Met Pro
                325                 330                 335
Gly Asp Val Pro Val Cys Ser Pro Gln Gln Tyr Lys Asn Cys Ala His
            340                 345                 350
Pro Ala Ile Asp Ala Met Leu Arg Lys Asp Ser Cys Ala Cys Pro Asn
        355                 360                 365
Pro Cys Ala Ser Thr Arg Tyr Ala Lys Glu Leu Ser Met Val Arg Ile
    370                 375                 380
Pro Ser Arg Ala Ala Arg Phe Leu Ala Arg Lys Leu Asn Arg Ser
385                 390                 395                 400
Glu Ala Tyr Ile Ala Glu Asn Val Leu Ala Leu Asp Ile Phe Phe Glu
                405                 410                 415
Ala Leu Asn Tyr Glu Thr Val Glu Gln Lys Lys Ala Tyr Glu Met Ser
            420                 425                 430
Glu Leu Leu Gly Asp Ile Gly Gly Gln Met Gly Leu Phe Ile Gly Ala
        435                 440                 445
Ser Leu Leu Thr Ile Leu Glu Ile Leu Asp Tyr Leu Cys Glu Val Phe
    450                 455                 460
Arg Asp Lys Val Leu Gly Tyr Phe Trp Asn Arg Gln His Ser Gln Arg
465                 470                 475                 480
His Ser Ser Thr Asn Leu Leu Gln Glu Gly Leu Gly Ser His Arg Thr
                485                 490                 495
Gln Val Pro His Leu Ser Leu Gly Pro Arg Pro Thr Pro Pro Cys
            500                 505                 510
```

Ala Val Thr Lys Thr Leu Ser Ala Ser His Arg Thr Cys Tyr Leu Val
            515                 520                 525

Thr Gln Leu
    530

<210> SEQ ID NO 2
<211> LENGTH: 1746
<212> TYPE: DNA
<213> ORGANISM: Homo sapiens

<400> SEQUENCE: 2

| | | | | | |
|---|---|---|---|---|---|
| agaattcggc | acgacggggt | tctggccatg | aagcccacct | caggcccaga | ggaggcccgg | 60 |
| cggccagcct | cggacatccg | cgtgttcgcc | agcaactgct | cgatgcacgg | gctgggccac | 120 |
| gtcttcgggc | caggcagcct | gagcctgcgc | cggggggatgt | gggcagcggc | cgtggtcctg | 180 |
| tcagtggcca | ccttcctcta | ccaggtggct | gagagggtgc | gctactacag | ggagttccac | 240 |
| caccagactg | ccctgatgga | gcgagaaagc | caccggctca | tcttcccggc | tgtcaccctg | 300 |
| tgcaacatca | acccactgcg | ccgctcgcgc | ctaacgccca | cgacctgca | ctgggctggg | 360 |
| tctgcgctgc | tgggcctgga | tcccgcagag | cacgccgcct | cctgcgcgc | cctgggccgg | 420 |
| cccccctgcac | cgcccggctt | catgcccagt | cccaccttg | acatggcgca | actctatgcc | 480 |
| cgtgctgggc | actccctgga | tgacatgctg | ctggactgtc | gcttccgtgg | ccaaccttgt | 540 |
| gggcctgaga | acttcaccac | gatcttcacc | cggatgggaa | agtgctacac | atttaactct | 600 |
| ggcgctgatg | gggcagagct | gctcaccact | actaggggtg | gcatgggcaa | tgggctggac | 660 |
| atcatgctgg | acgtgcagca | ggaggaatat | ctacctgtgt | ggagggacaa | tgaggagacc | 720 |
| ccgtttgagg | tggggatccg | agtgcagatc | cacagccagg | aggagccgcc | catcatcgat | 780 |
| cagctgggct | tggggggtgtc | cccgggctac | cagacctttg | tttcttgcca | gcagcagcag | 840 |
| ctgagcttcc | tgccaccgcc | ctgggcgat | tgcagttcag | catctctgaa | ccccaactat | 900 |
| gagccagagc | cctctgatcc | cctaggctcc | cccagcccca | gcccagccc | tccctatacc | 960 |
| cttatggggt | gtcgcctggc | ctgcgaaacc | cgctacgtgg | ctcggaagtg | cggctgccga | 1020 |
| atggtgtaca | tgccaggcga | cgtgccagtg | tgcagccccc | agcagtacaa | gaactgtgcc | 1080 |
| cacccggcca | tagatgccat | gcttcgcaag | gactcgtgcg | cctgccccaa | cccgtgcgcc | 1140 |
| agcacgcgct | acgccaagga | gctctccatg | gtgcggatcc | cgagccgcgc | cgccgcgcgc | 1200 |
| ttcctggccc | ggaagctcaa | ccgcagcgag | gcctacatcg | cggagaacgt | gctggccctg | 1260 |
| gacatcttct | ttgaggcccct | caactatgag | accgtggagc | agaagaaggc | ctatgagatg | 1320 |
| tcagagctgc | ttggtgacat | ggggggccag | atggggctgt | tcatcggggc | cagcctgctc | 1380 |
| accatcctcg | agatcctaga | ctacctctgt | gaggtgttcc | gagacaaggt | cctgggatat | 1440 |
| ttctggaacc | gacagcactc | ccaaaggcac | tccagcacca | atctgcttca | ggaagggctg | 1500 |
| ggcagccatc | gaacccaagt | tccccacctc | agcctgggcc | ccagacctcc | cacccctccc | 1560 |
| tgtgccgtca | ccaagactct | ctccgcctcc | caccgcacct | gctaccttgt | cacacagctc | 1620 |
| tagacctgct | gtctgtgtcc | tcggagcccc | gccctgacat | cctggacatg | cctagcctgc | 1680 |
| acgtagcttt | tccgtcttca | ccccaaataa | agtcctaatg | catcaaaaaa | aaaaaaaaa | 1740 |
| aaaaaa | | | | | | 1746 |

<210> SEQ ID NO 3
<211> LENGTH: 549
<212> TYPE: PRT
<213> ORGANISM: Homo sapiens

<400> SEQUENCE: 3

```
Met Lys Pro Thr Ser Gly Pro Glu Glu Ala Arg Arg Pro Ala Ser Asp
 1               5                  10                  15
Ile Arg Val Phe Ala Ser Asn Cys Ser Met His Gly Leu Gly His Val
             20                  25                  30
Phe Gly Pro Gly Ser Leu Ser Leu Arg Arg Gly Met Trp Ala Ala Ala
         35                  40                  45
Val Val Leu Ser Val Ala Thr Phe Leu Tyr Gln Val Ala Glu Arg Val
 50                  55                  60
Arg Tyr Tyr Arg Glu Phe His His Gln Thr Ala Leu Asp Glu Arg Glu
65                  70                  75                  80
Ser His Arg Leu Ile Phe Pro Ala Val Thr Leu Cys Asn Ile Asn Pro
                 85                  90                  95
Leu Arg Arg Ser Arg Leu Thr Pro Asn Asp Leu His Trp Ala Gly Ser
            100                 105                 110
Ala Leu Leu Gly Leu Asp Pro Ala Glu His Ala Ala Phe Leu Arg Ala
        115                 120                 125
Leu Gly Arg Pro Pro Ala Pro Pro Gly Phe Met Pro Ser Pro Thr Phe
    130                 135                 140
Asp Met Ala Gln Leu Tyr Ala Arg Ala Gly His Ser Leu Asp Asp Met
145                 150                 155                 160
Leu Leu Asp Cys Arg Phe Arg Gly Gln Pro Cys Gly Pro Glu Asn Phe
                165                 170                 175
Thr Thr Ile Phe Thr Arg Met Gly Lys Cys Tyr Thr Phe Asn Ser Gly
            180                 185                 190
Ala Asp Gly Ala Glu Leu Leu Thr Thr Thr Arg Gly Gly Met Gly Asn
        195                 200                 205
Gly Leu Asp Ile Met Leu Asp Val Gln Gln Glu Glu Tyr Leu Pro Val
    210                 215                 220
Trp Arg Asp Asn Glu Glu Thr Pro Phe Glu Val Gly Ile Arg Val Gln
225                 230                 235                 240
Ile His Ser Gln Glu Glu Pro Pro Ile Ile Asp Gln Leu Gly Leu Gly
                245                 250                 255
Val Ser Pro Gly Tyr Gln Thr Phe Val Ser Cys Gln Gln Gln Gln Leu
            260                 265                 270
Ser Phe Leu Pro Pro Pro Trp Gly Asp Cys Ser Ser Ala Ser Leu Asn
        275                 280                 285
Pro Asn Tyr Glu Pro Glu Pro Ser Asp Pro Leu Gly Ser Pro Ser Pro
    290                 295                 300
Ser Pro Ser Pro Pro Tyr Thr Leu Met Gly Cys Arg Leu Ala Cys Glu
305                 310                 315                 320
Thr Arg Tyr Val Ala Arg Lys Cys Gly Cys Arg Met Val Tyr Met Pro
                325                 330                 335
Gly Asp Val Pro Val Cys Ser Pro Gln Gln Tyr Lys Asn Cys Ala His
            340                 345                 350
Pro Ala Ile Asp Ala Met Leu Arg Lys Asp Ser Cys Ala Cys Pro Asn
        355                 360                 365
Pro Cys Ala Ser Thr Arg Tyr Ala Lys Glu Leu Ser Met Val Arg Ile
    370                 375                 380
Pro Ser Arg Ala Ala Arg Phe Leu Ala Arg Lys Leu Asn Arg Ser
385                 390                 395                 400
Glu Ala Tyr Ile Ala Glu Asn Val Leu Ala Leu Asp Ile Phe Phe Glu
                405                 410                 415
```

-continued

```
Ala Leu Asn Tyr Glu Thr Val Glu Gln Lys Lys Ala Tyr Glu Met Ser
            420                 425                 430

Glu Leu Leu Gly Asp Ile Gly Gly Gln Met Gly Leu Phe Ile Gly Ala
        435                 440                 445

Ser Leu Leu Thr Ile Leu Glu Ile Leu Asp Tyr Leu Cys Glu Val Phe
    450                 455                 460

Arg Asp Lys Val Leu Gly Tyr Phe Trp Asn Arg Gln His Ser Gln Arg
465                 470                 475                 480

His Ser Ser Thr Asn Leu Leu Gln Glu Gly Leu Gly Ser His Arg Thr
                485                 490                 495

Gln Val Pro His Leu Ser Leu Gly Pro Ser Thr Leu Leu Cys Ser Glu
            500                 505                 510

Asp Leu Pro Pro Leu Pro Val Pro Ser Pro Arg Leu Ser Pro Pro Pro
        515                 520                 525

Thr Ala Pro Ala Thr Leu Ser His Ser Ser Arg Pro Ala Val Cys Val
    530                 535                 540

Leu Gly Ala Pro Pro
545
```

<210> SEQ ID NO 4
<211> LENGTH: 1766
<212> TYPE: DNA
<213> ORGANISM: Homo sapiens

<400> SEQUENCE: 4

```
agaattcggc acgacggggt tctggccatg aagcccacct caggcccaga ggaggcccgg     60
cggccagcct cggacatccg cgtgttcgcc agcaactgct cgatgcacgg gctgggccac    120
gtcttcgggc aggcagcct gagcctgcgc cgggggatgt gggcagcggc cgtggtcctg    180
tcagtggcca ccttcctcta ccaggtggct gagagggtgc gctactacag ggagttccac    240
caccagactg ccctgatga gcgagaaagc caccggctca tcttcccggc tgtcaccctg    300
tgcaacatca ccccactgcg ccgctcgcgc ctaacgccca cgacctgca ctgggctggg    360
tctgcgctgc tgggcctgga tcccgcagag cacgccgcct cctgcgcgc cctgggccgg    420
cccctgcac cgcccggctt catgcccagt cccaccttg acatggcgca actctatgcc    480
cgtgctgggc actccctgga tgacatgctg ctggactgtc gcttccgtgg ccaaccttgt    540
gggcctgaga acttcaccac gatcttcacc cggatgggaa agtgctacac atttaactct    600
ggcgctgatg gggcagagct gctcaccact actaggggtg gcatgggcaa tgggctggac    660
atcatgctgg acgtgcagca ggaggaatat ctacctgtgt ggagggacaa tgaggagacc    720
ccgtttgagg tggggatccg agtgcagatc cacagccagg aggagccgcc catcatcgat    780
cagctgggct tgggggtgtc cccgggctac agaccctttg ttcttgcca gcagcagcag    840
ctgagcttcc tgccaccgcc ctggggcgat tgcagttcag catctctgaa ccccaactat    900
gagccagagc cctctgatcc cctaggctcc ccagccccca gccccagccc tccctatacc    960
cttatggggt gtcgcctggc ctgcgaaacc cgctacgtgg ctcggaagtg cggctgccga   1020
atggtgtaca tgccaggcga cgtgccagtg tgcagccccc agcagtacaa gaactgtgcc   1080
caccccggcca tagatgccat gcttcgcaag gactcgtgcg cctgccccaa cccgtgcgcc   1140
agcacgcgct acgccaagga gctctccatg gtgcggatcc cgagccgcgc cgccgcgcgc   1200
ttcctggccc ggaagctcaa ccgcagcgag gcctacatcg cggagaacgt gctggccctg   1260
gacatcttct tgaggcccct caactatgag accgtggagc agaagaaggc ctatgagatg   1320
```

-continued

```
tcagagctgc ttggtgacat tgggggccag atggggctgt tcatcgggggc cagcctgctc    1380 accatcctcg agatcctaga ctacctctgt gaggtgttcc gagacaaggt cctgggatat    1440
ttctggaacc gacagcactc ccaaaggcac tccagcacca atctgcttca ggaagggctg    1500
ggcagccatc gaacccaagt tccccacctc agcctgggcc ccagcactct gctctgttcc    1560
gaagacctcc caccctccc tgtgccgtca ccaagactct ctccgcctcc caccgcacct    1620
gctaccttgt cacacagctc tagacctgct gtctgtgtcc tcggagcccc gcctgacat    1680 cctggacatg cctagcctgc acgtagcttt tccgtcttca ccccaaataa agtcctaatg    1740
catcaaaaaa aaaaaaaaaa aaaaaa                                          1766
```

<210> SEQ ID NO 5
<211> LENGTH: 543
<212> TYPE: PRT
<213> ORGANISM: Homo sapiens

<400> SEQUENCE: 5

```
Met Lys Pro Thr Ser Gly Pro Glu Glu Ala Arg Arg Pro Ala Ser Asp
 1               5                  10                  15

Ile Arg Val Phe Ala Ser Asn Cys Ser Met His Gly Leu Gly His Val
            20                  25                  30

Phe Gly Pro Gly Ser Leu Ser Leu Arg Arg Gly Met Trp Ala Ala Ala
        35                  40                  45

Val Val Leu Ser Val Ala Thr Phe Leu Tyr Gln Val Ala Glu Arg Val
    50                  55                  60

Arg Tyr Tyr Arg Glu Phe His His Gln Thr Ala Leu Asp Glu Arg Glu
65                  70                  75                  80

Ser His Arg Leu Ile Phe Pro Ala Val Thr Leu Cys Asn Ile Asn Pro
                85                  90                  95

Leu Arg Arg Ser Arg Leu Thr Pro Asn Asp Leu His Trp Ala Gly Ser
            100                 105                 110

Ala Leu Leu Gly Leu Asp Pro Ala Glu His Ala Ala Phe Leu Arg Ala
        115                 120                 125

Leu Gly Arg Pro Pro Ala Pro Pro Gly Phe Met Pro Ser Pro Thr Phe
    130                 135                 140

Asp Met Ala Gln Leu Tyr Ala Arg Ala Gly His Ser Leu Asp Asp Met
145                 150                 155                 160

Leu Leu Asp Cys Arg Phe Arg Gly Gln Pro Cys Gly Pro Glu Asn Phe
                165                 170                 175

Thr Thr Ile Phe Thr Arg Met Gly Lys Cys Tyr Thr Phe Asn Ser Gly
            180                 185                 190

Ala Asp Gly Ala Glu Leu Leu Thr Thr Thr Arg Gly Gly Met Gly Asn
        195                 200                 205

Gly Leu Asp Ile Met Leu Asp Val Gln Gln Glu Glu Tyr Leu Pro Val
    210                 215                 220

Trp Arg Asp Asn Glu Glu Thr Pro Phe Glu Val Gly Ile Arg Val Gln
225                 230                 235                 240

Ile His Ser Gln Glu Glu Pro Pro Ile Ile Asp Gln Leu Gly Leu Gly
                245                 250                 255

Val Ser Pro Gly Tyr Gln Thr Phe Val Ser Cys Gln Gln Gln Gln Leu
            260                 265                 270

Ser Phe Leu Pro Pro Pro Trp Gly Asp Cys Ser Ser Ala Ser Leu Asn
        275                 280                 285
```

```
Pro Asn Tyr Glu Pro Glu Pro Ser Asp Pro Leu Gly Ser Pro Ser Pro
    290                 295                 300
Ser Pro Ser Pro Pro Tyr Thr Leu Met Gly Cys Arg Leu Ala Cys Glu
305                 310                 315                 320
Thr Arg Tyr Val Ala Arg Lys Cys Gly Cys Arg Met Val Tyr Met Pro
                325                 330                 335
Gly Asp Val Pro Val Cys Ser Pro Gln Gln Tyr Lys Asn Cys Ala His
            340                 345                 350
Pro Ala Ile Asp Ala Met Leu Arg Lys Asp Ser Cys Ala Cys Pro Asn
        355                 360                 365
Pro Cys Ala Ser Thr Arg Tyr Ala Lys Glu Leu Ser Met Val Arg Ile
    370                 375                 380
Pro Ser Arg Ala Ala Ala Arg Phe Leu Ala Arg Lys Leu Asn Arg Ser
385                 390                 395                 400
Glu Ala Tyr Ile Ala Glu Asn Val Leu Ala Leu Asp Ile Phe Phe Glu
                405                 410                 415
Ala Leu Asn Tyr Glu Thr Val Glu Gln Lys Lys Ala Tyr Glu Met Ser
            420                 425                 430
Glu Leu Leu Gly Asp Ile Gly Gly Gln Met Gly Leu Phe Ile Gly Ala
        435                 440                 445
Ser Leu Leu Thr Ile Leu Glu Ile Leu Asp Tyr Leu Cys Glu Val Phe
    450                 455                 460
Arg Asp Lys Val Leu Gly Tyr Phe Trp Asn Arg Gln His Ser Gln Arg
465                 470                 475                 480
His Ser Ser Thr Asn Leu Thr Ser His Pro Ser Leu Cys Arg His Gln
                485                 490                 495
Asp Ser Leu Arg Leu Pro Pro His Leu Leu Pro Cys His Thr Ala Leu
            500                 505                 510
Asp Leu Leu Ser Val Ser Ser Glu Pro Arg Pro Asp Ile Leu Asp Met
        515                 520                 525
Pro Ser Leu His Val Ala Phe Pro Ser Ser Pro Gln Ile Lys Ser
    530                 535                 540

<210> SEQ ID NO 6
<211> LENGTH: 1671
<212> TYPE: DNA
<213> ORGANISM: Homo sapiens

<400> SEQUENCE: 6
agaattcggc acgacggggt tctggccatg aagcccacct caggcccaga ggaggcccgg      60
cggccagcct cggacatccg cgtgttcgcc agcaactgct cgatgcacgg gctgggccac     120
gtcttcgggc aggcagcct  gagcctgcgc cggggggatgt gggcagcggc cgtggtcctg     180
tcagtggcca ccttcctcta ccaggtggct gagagggtgc gctactacag ggagttccac     240
caccagactg ccctggatga gcgagaaagc caccggctca tcttcccggc tgtcaccctg     300
tgcaacatca acccactgcg ccgctcgcgc ctaacgccca cgacctgca  ctgggctggg     360 tctgcgctgc tgggcctgga tcccgcagag cacgccgcct cctgcgcgc  cctgggccgg     420 ccccctgcac cgcccggctt catgcccagt cccacctttg acatggcgca actctatgcc     480
cgtgctgggc actccctgga tgacatgctg ctggactgtc gcttccgtgg ccaaccttgt     540
gggcctgaga acttcaccac gatcttcacc cggatgggaa agtgctacac atttaactct     600
ggcgctgatg gggcagagct gctcaccact actaggggtg gcatgggcaa tgggctggac     660
atcatgctgg acgtgcagca ggaggaatat ctacctgtgt ggagggacaa tgaggagacc     720
```

-continued

```
ccgtttgagg tggggatccg agtgcagatc cacagccagg aggagccgcc catcatcgat      780
cagctgggct tgggggtgtc cccgggctac cagacctttg tttcttgcca gcagcagcag      840
ctgagcttcc tgccaccgcc ctggggcgat tgcagttcag catctctgaa ccccaactat      900
gagccagagc cctctgatcc cctaggctcc cccagcccca gcccagccc tccctatacc       960 cttatggggt gtcgcctggc ctgcgaaacc cgctacgtgg ctcggaagtg cggctgccga     1020
atggtgtaca tgccaggcga cgtgccagtg tgcagccccc agcagtacaa gaactgtgcc     1080
cacccggcca tagatgccat gcttcgcaag gactcgtgcg cctgccccaa cccgtgcgcc     1140
agcacgcgct acgccaagga gctctccatg gtgcggatcc cgagccgcgc cgccgcgcgc     1200
ttcctggccc ggaagctcaa ccgcagcgag gcctacatcg cggagaacgt gctggccctg     1260
gacatcttct ttgaggccct caactatgag accgtggagc agaagaaggc ctatgagatg     1320
tcagagctgc ttggtgacat tgggggccag atggggctgt catcggggc cagcctgctc      1380 accatcctcg agatcctaga ctacctctgt gaggtgttcc gagacaaggt cctgggatat     1440
ttctggaacc gacagcactc ccaaaggcac tccagcacca atctgacctc ccaccctcc     1500 ctgtgccgtc accaagactc tctccgcctc ccaccgcacc tgctaccttg tcacacagct     1560
ctagacctgc tgtctgtgtc ctcggagccc cgccctgaca tcctggacat gcctagcctg     1620
cacgtagctt ttccgtcttc accccaaata aagtcctaat gcatcaaaaa a             1671
```

<210> SEQ ID NO 7
<211> LENGTH: 51
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 26
<223> OTHER INFORMATION: n = c or t

<400> SEQUENCE: 7

```
ctccctgtgc cgtcaccaag actctntccg cctcccaccg cacctgctac c              51
```

<210> SEQ ID NO 8
<211> LENGTH: 51
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 26
<223> OTHER INFORMATION: n = a or g

<400> SEQUENCE: 8

```
gaatatctac ctgtgtggag ggacantggt agggagcaca caaatgaggc t              51
```

<210> SEQ ID NO 9
<211> LENGTH: 88
<212> TYPE: PRT
<213> ORGANISM: Artificial Sequence
<220> FEATURE:
<223> OTHER INFORMATION: Synthetically generated peptide

<400> SEQUENCE: 9

```
Ala Pro Glu Thr Gly Thr Ala Cys Ser Cys Gly Asn Ser Lys Gly Ile
  1               5                  10                  15

Tyr Trp Phe Tyr Arg Pro Ser Cys Pro Thr Asp Arg Gly Tyr Thr Gly
             20                  25                  30
```

-continued

```
Ser Cys Arg Tyr Phe Leu Gly Thr Cys Cys Thr Pro Ala Asp Gly Thr
        35                  40                  45

Ala Cys Ser Cys Gly Asn Ser Lys Gly Ile Tyr Trp Phe Tyr Arg Pro
 50                  55                  60

Ser Cys Pro Thr Asp Arg Gly Tyr Thr Gly Ser Cys Arg Tyr Phe Leu
 65                  70                  75                  80

Gly Thr Cys Cys Thr Pro Ala Asp
             85
```

```
<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tttcacctgt cttggctcct                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
caggatagtg gtggggattg                                              20

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggagccaaac gggtcatcat ctc                                          23

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
gaggggccat ccacagtctt ct                                           22

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gccaacttcc gtagcttcaa g                                            21

<210> SEQ ID NO 15
<211> LENGTH: 21
<212> TYPE: DNA
<213> ORGANISM: Artificial Sequence
<220> FEATURE:
<223> OTHER INFORMATION: Primer
```

```
<400> SEQUENCE: 15
taccgcgtga agaccacttt g                                              21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
tgctcgggtt ggatgagagt g                                              21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
ggagcaatag agcagcatgt c                                              21

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ccgaagcagt tcagcatgct ggag                                           24

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
atcctcgcct gagttaaaca tg                                             22

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
tgccgccgcg ccacttcgag g                                              21

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
atcctcgcct gagttaaaca tg                                             22
```

```
<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
tctggcaaca ctctgctcca ggaag                                    25

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
actgggagcg gtaggaggcc tg                                       22

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gggtgacaca ggacagtcag                                          20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cagccaaggt ctgaaaggtc                                          20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ccctggtttt gctgatgctg                                          20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ttcccacagg agaagacaaa c                                        21

<210> SEQ ID NO 28
<211> LENGTH: 20
<212> TYPE: DNA
<213> ORGANISM: Artificial Sequence
<220> FEATURE:
<223> OTHER INFORMATION: Primer
```

```
<400> SEQUENCE: 28
tccactggtg ttgagacgcc                                               20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ctttgaactc gctgtcagtc                                               20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gtgacctccc caaaagtaga                                               20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
acaggagtct ctgcttccag                                               20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gccacctgtg tgactcatcg                                               20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
ggcttcagag cccacattgg                                               20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
attgcatcaa gcaagtgcag                                               20
```

```
<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gagccgtcaa acaggaagag                                                   20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ctggaaagca cttgggtcat                                                   20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ggagacagaa tgcacaagca                                                   20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
acgacaggaa ggtgaagagc                                                   20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
aaatttccat ccaggcctct                                                   20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
ctaacccatg cgagaacgat                                                   20

<210> SEQ ID NO 41
<211> LENGTH: 20
<212> TYPE: DNA
<213> ORGANISM: Artificial Sequence
<220> FEATURE:
<223> OTHER INFORMATION: Primer
```

```
<400> SEQUENCE: 41
cttgcacaga cactcgaagc                                               20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
ctgagtgtgg ctgtgaggag                                               20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
caggtctgac aacgggagat                                               20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
cctgtcaatc cagacccagt                                               20

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
tgtcatgggc tttcctctct g                                             21

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
ggcccttgta acaacaaaa tac                                            23

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
ggcaacaaga gctgacagta aat                                           23
```

```
<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
actccagcgt cgccatcagg attct                                         25

<210> SEQ ID NO 49
<211> LENGTH: 25
<212> TYPE: DNA
<213> ORGANISM: Artificial Sequence
<220> FEATURE:
<223> OTHER INFORMATION: Primer

<400> SEQUENCE: 49
taaacaggtg agactccagc aactt                                         25

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gttgcaagct ctcctgttcc                                               20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
tctctccagg agtgccatct                                               20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tctcctggct cttccacact                                               20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
ccacaatgat ggcagagatg                                               20

<210> SEQ ID NO 54
<211> LENGTH: 20
<212> TYPE: DNA
<213> ORGANISM: Artificial Sequence
<220> FEATURE:
<223> OTHER INFORMATION: Primer
```

```
<400> SEQUENCE: 54
tggaggctgt tggtagtgag                                                        20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
tcttagggaa ccgaatcacc                                                        20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ggaatcagct ctgtggacct                                                        20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
tgggtcagct cttgtgaatg                                                        20

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
ctcctgttga cccagagcat g                                                      21

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gtggagcaga aatgctggag                                                        20
```

TREATMENT OF INSULIN RESISTANCE

BACKGROUND

Insulin resistance or glucose intolerance is a condition characterized by the body's inability to properly use insulin or blood sugar. In this condition, normal amounts of insulin are inadequate to produce a normal insulin response from fat, muscle, or liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often lead to the metabolic syndrome, such as abdominal obesity, atherogenic dyslipidemia, elevated blood pressure, prothrombotic state (e.g., high fibrinogen or plasminogen activator inhibitor-1 in the blood), and proinflammatory state (e.g., elevated C-reactive protein in the blood). People with the metabolic syndrome are at increased risk of cardiovascular diseases and type 2 diabetes. The metabolic syndrome has become increasingly common in the United States. There is a need for effective treatment of insulin resistance.

SUMMARY

This invention relates to treating insulin resistance and identifying a compound for treating insulin resistance.

In one aspect, the invention features a method of identifying a compound for treating insulin resistance. The method includes contacting a first cell expressing an acid-sensing ion channel 3 (ASIC3) with a test compound, and determining an expression or activity level of the acid-sensing ion channel 3 in the cell. The test compound is determined to be a candidate compound for treating insulin resistance if the expression or activity level is lower than that determined in the same manner from a second cell except that the second cell is not contacted with the compound. The activity of the acid-sensing ion channel 3 can be determined by electrophysical analysis. The ion channel activity of the acid-sensing ion channel 3 can be determined by whole-cell patch recording, a voltage-sensitive dye, an ion-sensitive dye, or a cytotoxicity assay. The method can further include administering the candidate compound to a non-human animal to confirm an efficacy thereof to treat insulin-resistance. The first cell or second cell can also be a non-neuronal and AdiproR2$^+$ cell. Examples of the cells include NIH3T3 cells, NIH3T3 L1 cells, differentiated NIH3T3 L1 cells, adipose cells, and fibroblast cells. The first cell or second cell can be positive for one or more of FAS, FGF10, aP2, ETO, PPARγ, and AdipoR1. In one example, the first or second cell is an adipose tissue cell, such as a white adipose tissue cell.

In another aspect, the invention features a method of treating insulin resistance, The method includes identifying a subject suffering from or being at risk for developing insulin resistance; inhibiting acid-sensing ion channel 3 in the subject; determining an expression or activity level of the acid-sensing ion channel 3 in a sample obtained from the subject before or after the inhibiting step; and comparing the level with a control level to confirm inhibition. The inhibiting step can be conducted by administering to the subject an effective amount of a polypeptide that binds to the acid-sensing ion channel 3 or a nucleic acid that decreases the expression level of the acid-sensing ion channel 3. The control level can be obtained from a normal subject.

The invention further features a method of treating insulin resistance. The method includes identifying a subject suffering from or being at risk for developing insulin resistance, and administering to the subject an effective amount of an inhibitor of an acid-sensing ion channel 3. The inhibitor can be a polypeptide that binds to the acid-sensing ion channel 3 or a nucleic acid that decreases the expression level of the acid-sensing ion channel 3. For example, the inhibitor is an antibody or an antisense nucleic acid or an RNAi agent The control level is obtained from a normal subject.

The invention also features a method for acute treatment of insulin resistance. The method includes identifying a subject suffering from or being at risk for developing insulin resistance, and administering to the subject, within an hour of food ingestion, an effective amount of an inhibitor of an acid-sensing ion channel 3.

The inhibitor can be a polypeptide that binds to the acid-sensing ion channel 3 or a nucleic acid that decreases the expression level of the acid-sensing ion channel 3. For example, the inhibitor is an antibody or an antisense nucleic acid or an RNAi agent. The control level is obtained from a normal subject.

The details of one or more embodiments of the invention are set forth in the accompanying description below. Other features, objects, and advantages of the invention will be apparent from the detailed description, and from the claims.

DETAILED DESCRIPTION

This invention is based, at least in part, on the unexpected discoveries that ASIC3−/− mice were protected against age-dependent glucose intolerance with enhanced insulin sensitivity and that age-dependent glucose intolerance was associated with the up-regulation of ASIC3 expressed in white adipose tissue (WAT) but not sensory neurons.

Acid-sensing ion channels (ASICs) mediate inward currents and depolarize cells when the extracellular pH drops (Krishtal, 2003, Trends Neurosci. 26, s477-483). They belong to the epithelial sodium channel/degenerin superfamily, which are characterized by two membrane-spanning domains with intracellular N- and C-termini and a large extracellular loop (Waldmann and Laadunski, 1998, Curr. Opin. Neurobiol. 8, 418-424 and Kellenberger and Schild, 2002, Physiol. Rev. 82, 735-767). There are seven ASIC subunits, including ASIC1a, ASIC1b, ASIC2a, ASIC2b, ASIC3, ASIC4, and ASIC5, which are encoded by five genes. Multiple subunits assemble to form a functional ion channel. Homomeric or heteromeric ASICs has various sensitivity to extracellular pH, ranging from near physiological pH (~pH 7.0 for ASIC3) to very acidic status (~pH 5.0 for ASIC2a). ASICs express throughout neurons of mammalian central and peripheral nervous systems (Krishtal, 2003, Trends Neurosci. 26, 477-483). Accordingly, the role of ASICs has been implicated in detecting tissue acidosis, ischemia, and modulating synaptic activity (Molliver et al., 2005, Molecular Pain 1, 35, and Xiong et al, 2004, Cell 118, 687-698).

ASIC3 is the most sensitive acid-sensing ion channel ($pH_{0.5}$ activation ~6.7) and predominantly expressed in primary sensory neurons, especially in metaboreceptive sensory neurons or ischemia-sensing neurons (Waldmann and Lasdunski, 1998, Curr. Opin. Neurobiol. 8, 418-424). It responds better to lactic acid than to other acids to depolarize ischemia-sensing neurons. Therefore, ASIC3-expressing neurons might function as metaboreceptors to sense the anaerobic metabolism of tissues and trigger acid-linked pain sensation in muscle and heart (Molliver et al., 2005, Molecular Pain 1, 35).

The invention features a method for identifying an inhibitor of ASIC3 for treating insulin resistance. An ASIC3 inhibitor, which reduces ASIC3's expression level or channel activity in a statistically significant manner, can be identified according to the methods described below.

Candidate compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Pes. 12:145. Examples of methods for the synthesis of molecular libraries can be found in, e.g., DeWit et al., 1993, PNAS USA 90:6909; Erb et al., 1994, FNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carrell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify an ASIC3 inhibitor, one can contact a candidate compound with a system containing an ASIC3 gene or polypeptide. The system can be a cell-free system or a cell-containing system, e.g., an in vitro cell line model or an in vivo animal model. In a cell-containing system, cells can naturally express the ASIC3 gene, or can be modified to express a recombinant nucleic acid. The recombinant nucleic acid can contain the ASIC3 gene coding region fused to a heterologous promoter or an ASIC3 gene promoter sequence fused to a reporter gene. One then measures the expression level of the channel activity of ASIC3 polypeptide-containing channels.

An ASIC3 polypeptide described above refers to a full-length ASIC3 polypeptide or its functional equivalent. A functional equivalent refers to a polypeptide derived from the ASIC3 polypeptide, e.g., a fusion polypeptide or a polypeptide having one or more point mutations, insertions, deletions, truncations, or combination thereof. This polypeptide retains substantially activity of the ASIC3 polypeptide to formal functional channel, i.e., the ability to mediate inward currents and depolarize cells when the extracellular pH drops, as described above. Shown below are the amino acid and nucleotide sequences of various transcription variants and single nucleotide polymorphism (SNP) variants of ASIC3.

```
Transcript variant 1 (isoform a): 531 a.a.
ACCESSION NP_004760 (SEQ ID NO: 1)

1 MKPTSGPEEA RRPASDIRVF ASNCSMHGLG HVFGPGSLSL
      RRGMWAAAVV LSVATFLYQV

61 AERVRYYREF HHQTALDERE SHRLIFPAVT LCNINPLRRS
      RLTPNDLHWA GSALLGLDPA

121 EHAAFLRALG RPPAPPGFMP SPTFDMAQLY ARAGHSLDDM
      LLDCRFRGQP CGPENFTTIF
```

```
  181 TRMGKCYTFN SGADGAELLT TTRGGMGNGL DIMLDVQQEE
      YLPVWRDNEE TPFEVGIRVQ

241 IHSQEEPPII DQLGLGVSPG YQTFVSCQQQ QLSPLPPPWG
      DCSSASLNPN YEPEPSDPLG

301 SPSPSPSPPY TLMGCRLACE TRYVARKCGC RMVYMPGDVP
      VCSPQQYKNC AHPAIDAMLR

361 KDSCACPNPC ASTRYAKELS MVRIPSRAAA RFLARKLNRS
      EAYIAENVLA LDIFFEALNY

421 ETVEQKKAYE MSELLDGIGG QMGLFIGASL LTILEILDYL
      CEVFRDKVLG YFWNRQHSQR

481 HSSTNLLQEG LGSHRTQVPH LSLGPRPPTP PCAVTKTLSA
      SHRTCYLVTQ L

Transcript variant 1 (isoform a): 1746 bp
ACCESSION NM_004769 (SEQ ID NO: 2)

1 agaattcggc acgacggggt tctggccatg aagcccacct
      caggcccaga ggaggcccgg 61 cggccagcct cggacatccg cgtgttcgcc agcaactgct
      cgatgcacgg gctgggccac 121 gtcttcgggc caggcagcct gagcctgcgc cgggggatgt
      gggcagcggc cgtggtcctg 181 tcagtggcca ccttcctcta ccaggtggct gagagggtgc
      gctactacag ggagttccac 241 caccagactg ccctggatga gcgagaaagc caccggctca
      tcttcccggc tgtcaccctg 301 tgcaacatca acccactgcg ccgctcgcgc ctaacgccca
      acgacctgca ctgggctggg 361 tctgcgctgc tgggcctgga tcccgcagag cacgccgcct
      tcctgcgcgc cctgggccgg 421 cccctgcac cgcccggctt catgcccagt cccacctttg
      acatggcgca actctatgcc 481 cgtgctgggc actccctgga tgacatgctg ctggactgtc
      gcttccgtgg ccaaccttgt 541 gggcctgaga acttcaccac gatcttcacc cggatgggaa
      agtgctacac atttaactct 601 ggcgctgatg gggcagagct gctcaccact actagggtg
      gcatgggcaa tgggctggac 661 atcatgctgg acgtgcagca ggaggaatat ctacctgtgt
      ggagggacaa tgaggagacc 721 ccgtttgagg tggggatccg agtgcagatc cacagccagg
      aggagccgcc catcatcgat 781 cagctgggct tgggggtgtc cccgggctac cagacctttg
      tttcttgcca gcagcagcag 841 ctgagcttcc tgccaccgcc ctggggcgat tgcagttcag
      catctctgaa ccccaactat 901 gagccagagc cctctgatcc cctaggctcc cccagcccca
      gccccagccc tccctatacc 961 cttatgggt gtcgcctggc ctgcgaaacc cgctacgtgg
      ctgccaagtg cggctgccga 1021 atggtgtaca tgccaggcga cgtgccagtg tgcagccccc
      agcagtacaa gaactgtgcc 1081 cacccggcca tagatgccat gcttcgcaag gactcgtgcg
      cctgcccaa cccgtgcgcc 1141 agcacgcgct acgccaagga gctctccatg gtgcggatcc
      cgagccgcgc cgccgcgcgc
```

```
1201  ttcctggccc ggaagctcaa ccgcagcgag gcctacatcg
      cggagaacgt gctggccctg 1261  gacatcttct ttgaggccct caactatgag accgtggagc
      agaagaaggc ctatgagatg 1321  tcagagctgc ttggtgacat tggggggccag atggggctgt
      tcatcggggc cagcctgctc 1381  accatcctcg agatcctaga ctacctctgt gaggtgttcc
      gagacaaggt cctgggatat 1441  ttctggaacc gacagcactc ccaaaggcac tccagcacca
      atctgcttca ggaagggctg 1501  ggcagccatc gaacccaagt tccccacctc agcctgggcc
      ccagacctcc caccccctccc 1561  tgtgccgtca ccaagactct ctccgcctcc accgcacct
      gctaccttgt cacacagctc 1621  tagacctgct gtctgtgtcc tcggagcccc gccctgacat
      cctggacatg cctagcctgc 1681  acgtagcttt tccgtcttca ccccaaataa agtcctaatg
      catcaaaaaa aaaaaaaaaa 1741  aaaaaa
```

Transcript variant 2 (isoform b): 549 a.a.
ACCESSION NP_064717 (SEQ ID NO: 3)

```
  1  MKPTSGPEEA RRPASDIRVF ASNCSMHGLG HVFGPGSLSL
     RRGMWAAAVV LSVATFLYQV

61  AERVRYYREF HHQTALDERE SHRLIFPAVT LCNINPLRRS
     RLTPNDLHWA GSALLGLDPA

121  EHAAFLRALG RPPAPPGFMP SPTFDMAQLY ARAGHSLDDM
     LLDCRFRGQP CGPENFTTIF

181  TPMGKCYTFN SGADGAELLT TTRGGMGNGL DIMLDVQQEE
     YLPVWRDNEE TPPEVGIEVQ

241  IRSQEEPPII DQLGLGVSPG YQTFVSCQQQ QLSFLPPPWG
     DCSSASLNPN YEPEPSDPLG

301  SPSPSPSPPY TLMGCRLACE TRYVARKCGC RMVYMPGDVP
     VCSPQQYKNC AHPAIDAMLR

361  KDSCACPNPC ASTRYAKELS MVRIPSRAAA RFLARKLNRS
     EAYIAENVLA LDIFFEALNY

421  ETVEQKKAYE MSELLGDIGG QMGLFIGASL LTILEILDYL
     CEVFRDKVLG YFWNRQHSQR

481  HSSTNLLQEG LGSHRTQVPH LSLGPSTLLC SEDLPPLPVP
     SPRLSPPPTA PATLSHSSRP

541  AVCVLGAPP
```

Transcript variant 2 (isoform b): 1766 bp
ACCESSION NM_020321 (SEQ ID NO: 4)

```
  1  agaattcggc acgacgggt tctggccatg aagcccacct
     caggcccaga ggaggcccgg 61  cggccagcct cggacatccg cgtgttcgcc agcaactgct
     cgatgcacgg gctgggccac 121  gtcttcgggc caggcagcct gagcctgcgc cggggggatgt
     gggcagcggc cgtggtcctg 181  tcagtggcca ccttcctcta ccaggtggct gagagggtgc
     gctactacag ggagttccac 241  caccagactg ccctggatga gcgagaaagc caccggctca
     tcttcccggc tgtcaccctg
```

```
301  tgcaacatca cccactgcg ccgctcgcgc ctaacgccca
     acgacctgca ctgggctggg 361  tctgcgctgc tgggcctgga tcccgcagag cacgccgcct
     tcctgcgcgc cctgggccgg 421  cccccctgcac cgcccggctt catgcccagt cccacctttg
     acatggcgca actctatgcc 481  cgtgctgggc actccctgga tgacatgctg ctggactgtc
     gcttccgtgg ccaaccttgt 541  gggcctgaga acttcaccac gatcttcacc cggatgggaa
     agtgctacac atttaactct 601  ggcgctgatg gggcagagct gctcaccact actagggtg
     gcatgggcaa tgggctggac 661  atcatgctgg acgtgcagca ggaggaatat ctacctgtgt
     ggagggacaa tgaggagacc 721  ccgtttgagg tggggatccg agtgcagatc cacagccagg
     aggagccgcc catcatcgat 781  cagctgggct tgggggtgtc cccgggctac cagaccttg
     tttccttgcca gcagcagcag 841  ctgagcttcc tgccaccgcc ctggggcgat tgcagttcag
     catctctgaa ccccaactat 901  gagccagagc cctctgatcc cctaggctcc cccagccca
     gccccagccc tccctataccc 961  cttatggggt gtcgcctggc ctgcgaaacc cgctacgtgg
     ctcggaagtg cggctgccga 1021 atggtgtaca tgccaggcga cgtgccagtg tgcagccccc
     agcagtacaa gaactgtgcc 1081 cacccggcca tagatgccat gcttcgcaag gactcgtgcg
     cctgcccccaa cccgtgcgcc 1141 agcacgcgct acgccaagga gctctccatg gtgcggatcc
     cgagccgcgc cgccgcgcgc 1201 ttcctggccc ggaagctcaa ccgcagcgag gcctacatcg
     cggagaacgt gctggccctg 1261 gacatcttct ttgaggccct caactatgag accgtggagc
     agaagaaggc ctatgagatg 1321 tcagagctgc ttggtgacat tggggggccag atggggctgt
     tcatcggggc cagcctgctc 1381 accatcctcg agatcctaga ctacctctgt gaggtgttcc
     gagacaaggt cctgggatat 1441 ttctggaacc gacagcactc ccaaaggcac tccagcacca
     atctgcttca ggaagggctg 1501 ggcagccatc gaacccaagt tccccacctc agcctgggcc
     ccagcactct gctctgttcc 1561 gaagacctcc caccctccc tgtgccgtca ccaagactct
     ctccgcctcc accgcacct 1621 gctaccttgt cacacagctc tagacctgct gtctgtgtcc
     tcggagcccc gccctgacat 1681 cctggacatg cctagcctgc acgtagcttt tccgtcttca
     ccccaaataa agtcctaatg 1741 catcaaaaaa aaaaaaaaaa aaaaaa
```

Transcript variant 3 (isoform c): 543 a.a.
ACCESSION NP_064718 (SEQ ID NO: 5)

```
  1  MKPTSGPEEA RRPASDIRVF ASNCSMHGLG HVFGPGSLSL
     RRGMWAAAVV LSVATFLYQV
```

```
 61  AERVRYYREF HHQTALDERE SHRLIFPAVT LCNINPLRRS
     RLTPNDLHWA GSALLGLDPA

121  EHAAFLRALG RPPAPPGFMP SPTFDMAQLY ARAGHSLDDM
     LLDCRFRGQP CGPENFTTIF

181  TRMGKCYTFN SGADGAELLT TTRGGMGNGL DIMLDVQQEE
     YLPVWRDNEE TPFEVGIRVQ

241  IHSQEEPPII DQLGLGVSPG YQTFVSCQQQ QLSFLPPPWG
     DCSSASLNPN YEPEPSDPLG

301  SPSPSPSPPY TLMGCRLACE TRYVARKCGC RMVYMPGDVP
     VCSPQQYKNC AHPAIDAMLR

361  KDSCACPNPC ASTRYAKELS MVRIPSRAAA RFLARKLNRS
     EAYIAENVLA LDIFFEALNY

421  ETVEQKKAYE MSELLGDIGG QMGLFIGASL LTILEILDYL
     CEVFRDKVLG YFWNRQHSQR

481  HSSTNLTSHP SLCRHQDSLR LPPHLLPCHT ALDLLSVSSE
     PRPDILDMPS LHVAFPSSPQ

541  IKS

Transcript variant 3 (isoform c): 1671 bp
ACCESSION NM_020322 (SEQ ID NO: 6)

1  agaattcggc acgacgggt tctggccatg aagcccacct
     caggcccaga ggaggcccgg 61  cggccagcct cggacatccg cgtgttcgcc agcaactgct
     cgatgcacgg gctgggccac 121  gtcttcgggc caggcagcct gagcctgcgc cggggatgt
     gggcagcggc cgtggtcctg 181  tcagtggcca ccttcctcta ccaggtggct gagagggtgc
     gctactacag ggagttccac 241  caccagactg ccctggatga gcgagaaagc caccggctca
     tcttcccggc tgtcaccctg 301  tgcaacatca acccactgcg ccgctcgcgc ctaacgccca
     acgacctgca ctgggctggg 361  tctgcgctgc tgggcctgga tcccgcagag cacgccgcct
     tcctgcgcgc cctgggccgg 421  cccccctgcac cgccggctt catgcccagt cccaccttg
     acatggcgca actctatgcc 481  cgtgctgggc actccctgga tgacatgctg ctggactgtc
     gcttccgtgg ccaaccttgt 541  gggcctgaga acttcaccac gatcttcacc cggatgggaa
     agtgctacac atttaactct 601  ggcgctgatg gggcagagct gctcaccact actagggggtg
     gcatgggcaa tgggctggac
```

```
661  atcatgctgg acgtgcagca ggaggaatat ctacctgtgt
     ggagggacaa tgaggagacc 721  ccgtttgagg tggggatccg agtgcagatc cacagccagg
     aggagccgcc catcatcgat 781  cagctggggct tgggggtgtc cccgggctac cagacctttg
     tttcttgcca gcagcagcag 841  ctgagcttcc tgccaccgcc ctggggcgat gcagttcag
     catctctgaa ccccaactat 901  gagccagagc cctctgatcc cctaggctcc cccagcccca
     gccccagccc tcctatacc 961  cttatggggt gtcgcctggc ctgcgaaacc cgctacgtgg
     ctcggaagtg cggctgccga 1021 atggtgtaca tgccaggcga cgtgccagtg tgcagccccc
     agcagtacaa gaactgtgcc 1081 cacccggcca tagatgccat gcttcgcaag gactcgtgcg
     cctgccccaa cccgtgcgcc 1141 agcacgcgct acgccaagga gctctccatg gtgcggatcc
     cgagccgcgc cgccgcgc 1201 ttcctgcccc ggaagctcaa ccgcagcgag gcctacatcg
     cggagaacgt gctggccctg 1261 gacatcttct tgaggccct caactatgag accgtggagc
     agaagaaggc ctatgagatg 1321 tcagagctgc ttggtgacat tgggggccag atggggctgt
     tcatcggggc cagcctgctc 1381 accatcctcg agatcctaga ctacctctgt gaggtgttcc
     gagacaaggt cctgggatat 1441 ttctggaacc gacagcactc ccaaaggcac tccagcacca
     atctgacctc ccaccctcc 1501 ctgtgccgtc accaagactc tctccgcctc ccaccgcacc
     tgctaccttg tcacacagct 1561 ctagacctgc tgtctgtgtc ctcggagccc cgccctgaca
     tcctggacat gcctagcctg 1621 cacgtagctt tccgtcttc accccaaata aagtcctaat
     gcatcaaaaa a
```

SNP Variants of ASIC3

Cluster Report: rs3192795

(SEQ ID NO:7)
CTCCCTGTGCCGTCACCAAGACTCT [C/T] TCCGCCTCCCACCGCACC
TGCTACC

| Contig-->mRNA-->Protein | mRNA orientation | position | Function | dbSNP allele | Protein residue | Codon pos | Amino acid pos |
|---|---|---|---|---|---|---|---|
| NT_007914->NM_020321->NP_064717 | forward | 1595 | nonsynonymous | T | Phe [F] | 2 | 525 |
| | | | contig reference | C | Ser [S] | 2 | 525 |
| NT_007914->NM_020322->NP_064718 | forward | 1516 | nonsynonymous | T | Phe [F] | 1 | 499 |
| | | | contig reference | C | Leu [L] | 1 | 499 |

Cluster Report: rs1864545

(SEQ ID NO:8)
GAATATCTACCTGTGTGGAGGGACA [A/G] TGGTAGGGAGCACACAA
TGAGGCT

| Contig-->mRNA-->Protein | mRNA orientation | position | Function | dbSNP allele | Protein residue | Codon pos | Amino acid pos |
|---|---|---|---|---|---|---|---|
| NT_007914->NM_004769->NP_004760 | forward | 704 | nonsynonymous | G | Ser [S] | 2 | 228 |
|  |  |  | contig reference | A | Asn [N] | 2 | 228 |
| NT_007914->NM_020321->NP_064717 | forward | 704 | nonsynonymous | G | Ser [S] | 2 | 228 |
|  |  |  | contig reference | A | Asn [N] | 2 | 228 |
| NT_007914->NM_020322->NP_064718 | forward | 704 | nonsynonymous | G | Ser [S] | 2 | 228 |
|  |  |  | contig reference | A | Asn [N] | 2 | 228 |

3038-3049 (2005)), using ion-sensitive dyes and cytotoxicity assay (Weiser, J Neurosci Methods 137, 79-85 (2004).

To determine the ability of a candidate compound to inhibit ASIC3, one compares the level or activity obtained in the manner described above with a control level or activity obtained in the absence of the candidate compound. If the level or activity is lower than the control, the compound is identified as being effective for treating insulin resistance. One can further verify the efficacy of a compound thus-identified using an animal model. One can administer the compound to animal models and exam them according to the method describe below in the Example section or other standard techniques. Any statistically significant improvement of insulin sensitivity indicates the compound is a candidate for treating insulin resistance.

The invention also features methods for treating insulin resistance. A subject to be treated can be identified by standard diagnosing techniques for insulin resistance, such as diabetes. Optionally, the subject can then be examined for the gene expression or activity level of the ASIC3 polypeptide in adipose tissue cells (e.g., white adipose tissue cells) by methods described above. If the gene expression or channel activity level is higher in a sample from the subject than that in a sample from a normal person, the subject is a candidate for treatment with an effective amount of an ASIC3 inhibitor.

"Treating" refers to administration of a compound to a subject, who has insulin resistance, with the purpose to cure, alleviate, relieve, remedy, prevent, or ameliorate the disorder, the symptom of the disorder, the disease state secondary to the disorder, or the predisposition toward the disorder. An "effective amount" refers to an amount of the compound that is capable of producing a medically desirable result, e.g., as described above, in a treated subject. The treatment method can be performed in viva or ex vivo, alone or in conjunction with other drugs or therapy.

In an in viva approach, an ASIC3 inhibitor is administered to a subject. Generally, the compound is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. For treatment of insulin resistance, the compound can be delivered directly to white adipose tissues or surrounding tissues.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration.

The expression level can be determined at either the mRNA level oral the protein level. Methods of measuring mRNA levels in a cell, a tissue sample, or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE.

Methods of measuring protein levels in a cell, a tissue sample, or a body fluid are also known in the art. Many such methods employ antibodies (e.g., monoclonal or polyclonal antibodies) that bind specifically to a target protein. In such assays, the antibody itself or a secondary antibody that binds to if can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) can be used to enhance the sensitivity of the methodologies. Some of these protein-measuring assays (e.g., ELISA or Western blot) can be applied to body fluids or to lysates of cells, and others (e.g., immunohistological methods or fluorescence flow cytometry) applied to histological sections or unlysed cell suspensions. Methods of measuring the amount of label depend on the nature of the label and are well known in the art. Appropriate labels include radionuclides (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

Methods of measuring ASIC3's ion channel activity are also known in the art. Examples of the methods include using whole-cell patch recording (Waldmann et al., J Biol Chem 272, 20975-20978 (1997); Voilley et al., J Neurosci 21, 8026-8033 (2001); Molliver et at. Molecular Pain 1:35 (2005); using voltage-sensitive dye (Felix et al., Assay Drug Dev Technol. 2, 260-268 (2004); Sharma et al., Biophys J 88, For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Examples of compounds that can be used to treat insulin resistance include polypeptides such as APETx2 (GTAC-SCGNSKGIYWFYRPSCPTDRGYTGSCRY FLGTCCT-FAD) (SEQ ID NO:9) and its functional equivalents. A functional equivalent of APETx2 refers to a polypeptide derived from the APETx2 polypeptide, e.g., a fusion polypeptide or a polypeptide having one or more point mutations, insertions, deletions, truncations, or combination thereof. This polypeptide retains substantially activity of the APETx2 polypeptide, i.e., the ability to inhibit ASIC3 homomeric channels and ASIC3-containing heteromeric channels, as described in Diochot et al. EMBO J. 2004, 23(7): 1516-25.

The polypeptides can be synthesized using methods known in the art or be prepared using recombinant technology. For example, one can clone a nucleic acid encoding the polypeptide in an expression vector, in which the nucleic acid is operably linked to a regulatory sequence suitable for expressing the polypeptide in a host cell. One can then introduce the vector into a suitable host cell to express the polypeptide. The expressed recombinant polypeptide can be purified from the host cell by methods such as ammonium sulfate precipitation and fractionation column chromatography. See Goeddel, (1990) Gene Expression Technology: Methods in Enzymology 185, Academic Press, San Diego, Calif. A polypeptide thus prepared can be tested for its activity against ASIC3 homomeric channels and ASIC3-containing heteromeric channels according to the method described in the Example below or in Diochot et al. EMBO J. 2004, 23(7):1516-25.

Examples of compounds that can be used to treat insulin resistance also include antibodies that bind to polypeptides ASIC3 polypeptide. An "antibody" includes intact molecules as well as fragments thereof, such as Fab, F(ab')2, Fv, scFv (single chain antibody), and dAb (domain antibody; Ward, et al. (1989) Nature, 341, 544). A derivative of an antibody refers to a protein or a protein complex having a polypeptide variant of this invention. An antibody or derivative of this invention can be made by co-expressing corresponding light and heavy chain CDRs-containing polypeptides in a suitable host cell by methods known in the art. See, e.g., Harlow and Lane, (1988) Antibodies; A Laboratory Manual, Cold Spring Harbor Laboratory, New York.

To make an antibody described herein, ASIC3 polypeptide or its antigenic fragment can be coupled to a carrier protein, such as KLH, mixed with an adjuvant, and injected into a host animal. Antibodies produced in that animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies, heterogeneous populations of antibody molecules, are present in the sera of the immunized subjects. Monoclonal antibodies, homogeneous populations of antibodies to a particular antigen, can be prepared using standard hybridoma technology. See, e.g., Kohler et al. (1975) Nature 256, 495; Kohler et al. (1976) Eur. J. Immunol.6, 511; Kohler et al., (1976) Eur. J. Immunol. 6, 292; and Hammerling et al. (1981) Monoclonal Antibodies and T Cell Hybridomas, Elsevier, N.Y. In particular, monoclonal antibodies can be obtained by any technique that provides for the production of antibody molecules by continuous cell lines in culture such as described in U.S. Pat. No. 4,376,110; the human B-cell hybridoma technique (Kosbor et al. (1983) Immunol Today 4, 72; Cole et al. (1983) Proc. Natl. Acad. Sci. USA 80, 2026) and the EBV hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

A polynucleotide containing a nucleic acid sequence encoding an inhibitor of ASIC3 can be used to treat insulin resistance. The nucleic acid sequence can encode the above-described polypeptide, an anti-ASIC3 antibody, an anti-sense RNA, or a small interference RNA (e.g., an RNAi agent) that targets the ASIC3 and inhibits its expression or channel activity.

The term "RNAi" or "RNA interference" refers to a sequence-specific or selective process by which a target molecule (e.g., a target gene, protein or RNA) is down-regulated. Within the scope of this invention is utilization of RNAi featuring degradation, of RNA molecules (e.g., within a cell). Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free double-stranded RNA, which directs the degradative mechanism. Alternatively, RNAi can be initiated by the hand of man, for example, to silence the expression of target genes.

The term "RNAi agent" refers to an RNA (or analog thereof), having sufficient sequence complementarity to a target RNA (i.e., the RNA being degraded) to direct RNAi. A RNA agent having a "sequence sufficiently complementary to a target RNA sequence to direct RNAi" means that the RNA agent has a sequence sufficient to trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent can also have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence. The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

The polynucleotide can be delivered by the use of polymeric, biodegradable microparticle or microcapsule delivery devices known in the art. Another way to achieve uptake of the nucleic acid is using liposomes, prepared by standard methods. The polynucleotide can he incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

In the above-mentioned polynucleotides, e.g., expression vectors, the nucleic acid sequence encoding an inhibitor of ASIC3 is operatively linked to a promoter or enhancer-promoter combination. Suitable expression vectors include plasmids and viral vectors such as herpes viruses, retroviruses, vaccinia viruses, attenuated vaccinia viruses, canary pox viruses, adenoviruses and adeno-associated viruses.

As is well known in the art, the dosage for a patient depends upon various factors as described above. Dosages will vary, but a preferred dosage for administration of polynucleotide is about $10^6$ to $10^{12}$ copies of the polynucleotide molecule. This dose can be repeatedly administered as needed. Routes of administration can be any of those listed above.

Also within the scope of the invention is a packaged product including a container, an effective amount of an ASIC3 inhibitor and a legend associated with the container and indicating administration of the inhibitor for treating a subject suffering from or being at risk for developing insulin resistance. The inhibitor can be admixed with a pharmaceutically acceptable carrier, including a solvent, a dispersion medium, a coating, an antibacterial and antifungal agent, and an isotonic and absorption-delaying agent.

The inhibitor can be formulated into dosage forms for different administration routes utilizing conventional methods. For example, it can be formulated, in a capsule, a gel seal, or a tablet for oral administration. Capsules can contain any standard pharmaceutically acceptable materials such as gelatin or cellulose. Tablets can be formulated in accordance with conventional procedures by compressing mixtures of the inhibitor with a solid carrier and a lubricant. Examples of solid carriers include starch and sugar bentonite. The inhibitor can also be administered in a form of a hard shell tablet or a capsule containing a binder, e.g., lactose or mannitol, a conventional filler, and a tableting agent. The inhibitor can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent. Further, the inhibitor can be injected directly to the striatum via brain operation.

The efficacy of the inhibitor can be evaluated both in vitro and in vivo. For example, the inhibitor can be tested for its ability to repress gene expression or channel activity of ASIC3 in vitro. For in vivo studies, the inhibitor can be injected into an animal (e.g., an animal model) and its effects on insulin resistance are then accessed. Based on the results, an appropriate dosage range and administration route can be determined.

The above-described ASIC3 inhibitors, e.g., APETx2, are particular useful for acute treatment of insulin resistance, i.e., within one hour of food indigestion. For examples, a subject can receive 14 mg/kg of salicylic acid or 0.23 mg/kg of APETx2.

The above-described ASIC3 inhibitor, e.g., APETx2, can also be used in treating other diseases (e.g. obesity) that are associated with abnormally high level of ASIC3 gene expression or channel activity. A subject to be treated can be identified by methods known in the art or by determining the gene expression or channel activity level of the ASIC3 polypeptide in a sample prepared from a subject as described above. If the gene expression or channel activity level of the ASIC3 polypeptide is higher in the sample from the subject than that in a sample from a normal person, the subject is a candidate for treatment with an effective amount of an ASIC3 inhibitor.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE

Experimental Procedures

Mice

ASIC3−/− mice were generated as described in Chen et al., Proc. Natl. Acad. Sci. USA 99, 8992-8997, 2002. Congenic 129 mice were derived from breeding ASIC3 chimera with female 129S2/SvPasCrl wild type mice. All mice were raised in a 12:12-h light-dark cycle at 25° C. and 40% to 70% humidity. All experiments involved use of female mice in different age groups. The animals were bred in a specific pathogen-free facility and cared for in accordance with the *Guide for the Use of Laboratory Animals* (National Academy Press, Washington D.C.). The experimental protocol was approved by the animal use committee of Academia Sinica.

Primary Adipose Cell Culture and Immunostaining

Fat pads of periovarian white adipose tissue (WAT) were isolated from female mice. One gram of the isolated fat pad was digested with 2 mg/ml of collagenase type VIII (Sigma) in 4 ml Dulbeceo's modified Eagle's medium (DMEM) at 37° C. for 1 hour. Then, the digested tissues were centrifuged at 200xg for 5 minutes at 4° C. The supernatant, which contains mature adipocytes, was collected for RNA isolation. The cell pellet, the stromal-vascular fraction (SVF), consisted of mesenchynal cells (adipoblasts) and immature adipocytes (adipocyte precursors and postadipocytes) (Van, The adipocyte precursor cell. In: New perspectives in adipose tissue:structure, function, and development. Butterworths, Borough Green, England, chapt. 15, 353-382, 1985). The SVFs were collected for RNA isolation or re-suspended for cell culture in DMEM containing 10% fetal calf serum and antibiotics. SVF cells were plated at a concentration of $10^5$ cells per glass cover slide (12 mm in diameter) and maintained at 37° C. in 5% humidified carbon dioxide. The cultured cells then underwent whole-cell patch recording in 5 days.

For immunostaining, the cultured cells were fixed with icy methanol for 5 minutes, permeablized in 0.25% Triton X-100 for 5 minutes, and washed with PBS. The fixed cells were placed in a blocking solution containing 2% BSA, 0.2% Triton X-100 in PBS for 1 hour and incubated in a primary antibody solution (containing guinea pig anti-ASIC3 1:250 from Neuromics; rabbit anti-ACRP30 1:200 from Chemicon) overnight at 4° C. Then, the cells were washed 3 times for 3 minutes each in PBS and incubated with secondary antibodies diluted 1:200 in a blocking solution for 1 hour. Secondary antibodies were goat anti-guinea conjugated to Alexa Fluor 488 and anti-rabbit conjugated to Alexa Fluor 594 (Molecular Probes).

Real-Time Quantitative RT-PCR

Total RNA was isolated from frozen tissue, samples or isolated adipose cell fractions using the RNeasy kit (Qiagen). Total complementary DNA (cDNA) was synthesized from the total RNA using Superscript III RT (Invitrogen). Real-time polymerase chain reaction of individual cDNAs involved SYBR green dye to measure duplex DNA formation with the ABI Prism 7700 Sequence Detection System (PE Applied Biosystems) and normalized to the expression of GAPDH RNA. All the SYBR green core reagents and Ampli-Taq Gold polymerase were purchased from PE Applied Biosystems (Foster City, Calif.). The thermal cycling conditions were 95° C. for 10 minutes, followed by 40 cycles of 95° C. for 15 seconds and 60° C. for 1 minute. The primers used in the real-time RT-PCR were

```
ASIC3 sense,
5'-TTTCACCTGTCTTGGCTCCT-3'          (SEQ ID NO:10)

ASIC3 anti-sense,
5'-CAGGATAGTGGTGGGGATTG-3'          (SEQ ID NO:11)

GAPDH sense,
5'-GGAGCCAAACGGGTCATCATCTC-3'       (SEQ ID No:12)

GAPDH anti-sense,
5'-GAGGGGCCATCCACAGTCTTCT-3'.       (SEQ ID NO:13)
```

Electrophysiology of Adipose Cells

Whole cell recordings were made of primary culture adipose cells using a Multiclamp 700B amplifier (Axon instruments). Patch electrodes were pulled from thin-filament glass of 1.5 mm o.d. (Warner Instrument, Hamden, Conn., USA), and filled with a solution containing (in mM) KCl 100, EGTA 10, $MgCl_2$ 5, HEPES 40, $Na_2$-ATP 2, and $Na_3$-GTP 0.3 (pH adjusted to 7.4 with KOH and osmolarity to 300-310 mOsm). The electrodes had resistances of 2-5 MΩ when filled with this solution. Standard external solutions contained (in mM) NaCl 130, KCl 5, $MgCl_2$ 1, $CaCl_2$ 2, glucose 10, and Hepes 20 (pH 7.4 adjusted with NaOH). Once whole cell recordings were obtained, recordings were made in a Voltage-clamp mode, and ASIC3-mediated current was elicited by acid (pH 5.0 adjusted by MES) applied through a gravity-controlled perfusion system. Signals were low-pass filtered at a corner frequency of 3 kHz and then digitized online at a frequency of 10 kHz with use of a CED 1401 interface (Cambridge Electronic Design, The Science Park, Cambridge, UK) running Signal software provided by CED.

Single-Cell RT-PCR

After patch recordings, the adipose cells were picked up from the recording pipette and underwent single-cell RNA isolation. Total RNA of a single adipose cell was isolated by use of the Absolutely Nanoprep Kit (Strategene) according to the manufacture's guide.

The resulting total RNA was reverse-transcribed using Superscript III RT (Invitrogen). Then the quality of a small portion (1/60) of the resulting RT product underwent PCR to detect the expression of GAPDH RNA. One-sixth of the total RT solution was used as a template for multiplex PCR, which included the primer pair sets either for the ASIC family (including 7 ASIC subtypes, TRPV1, substance P, and CGRP), or adipose markers (including FAS, FGF10, aP2, DLK-1, SMAF1, ETO, UCP1, UCP3, ACRP30, adponectin receptor 1 & 2 (AdipoR1 and R2), PPARγ, and PPARγ2. The thermal cycling condition of multiplex PCR was 95° C. for 10 minutes, followed by 35 cycles of 95° C. for 15 seconds and 60° C. for 1 minute. The PCR products were the template (1/50volume) for nested PCR amplification to examine whether a specific gene was expressed in a single cell. Another set of primers, nested primers, were designed for the above-mentioned genes. The thermal cycling condition of the nested PCR was the same as for the multiplex PCR. After nested PCR amplification, the PCR products were analyzed in 4% agarose gel. The nested primers were

```
ASIC1a sense
5'-GCCAACTTCCGTAGCTTCAAG-3'         (SEQ ID NO:14)

ASIC1a antisense
5'- TACCGCGTGAAGACCACTTTG-3'        (SEQ ID NO:15)

ASIC1b sense
5'-TGCTCGGGTTGGATGAGAGTG-3'         (SEQ ID NO:16)

ASIC1b antisense
5'-GGAGCAATAGAGCAGCATGTC-3'         (SEQ ID NO:17)

ASIC2a sense
5'-CCGAAGCAGTTCAGCATGCTGGAG-3'      (SEQ ID NO:18)

ASIC2a antisense
5'-ATCCTCGCCTGAGTTAAACATG-3'        (SEQ ID NO:19)

ASIC2b sense
5'-TGCCGCCGCGCCACTTCGAGG-3'         (SEQ ID NO:20)

ASIC2b antisense
5'-ATCCTCGCCTGAGTTAAACATG-3'        (SEQ ID NO:21)

ASIC3 sense
5'-TCTGGCAACACTCTGCTCCAGGAAG-3'     (SEQ ID NO:22)

ASIC3 antisense
5'-ACTGGGAGCGGTAGGAGGCCTG-3'        (SEQ ID NO:23)

ASIC4 sense
5'-GGGTGACACAGGACAGTCAG-3'          (SEQ ID NO:24)

ASIC4 antisense
5'-CAGCCAAGGTCTGAAAGGTC-3'          (SEQ ID NO:25)

ASIC5 sense
5'-CCCTGGTTTTGCTGATGCTG-3'          (SEQ ID NO:26)

ASIC5 antisense
5'-TTCCCACAGGAGAAGACAAAC-3'         (SEQ ID NO:27)

TRPV1 sense
5'-TCCACTGGTGTTGAGACGCC-3'          (SEQ ID NO:28)

TRPV1 antisense
5'-CTTTGAACTCGCTGTCAGTC-3'          (SEQ ID NO:29)

Substance P sense
5'-GTGACCTCCCCAAAAGTAGA-3'          (SEQ ID NO:30)

Substance P sense antisense
5'-ACAGGAGTCTCTGCTTCCAG-3'          (SEQ ID NO:31)

CGRP sense
5'-GCCACCTGTGTGACTCATCG-3'          (SEQ ID NO:32)

CGRP antisense
5'-GGCTTCAGAGCCCACATTGG-3'          (SEQ ID NO:33)

FAS sense
5'-ATTGCATCAAGCAAGTGCAG-3'          (SEQ ID NO:34)
```

```
                          -continued
FAS antisense
5'-GAGCCGTCAAACAGGAAGAG-3'       (SEQ ID NO:35)

FGF10 sense
5'-CTGGAAAGCACTTGGGTCAT-3'       (SEQ ID NO:36)

FGF10 antisense
5'-GGAGACAGAATGCACAAGCA-3'       (SEQ ID NO:37)

aP2 sense
5'-ACGACAGGAAGGTGAAGAGC-3'       (SEQ ID NO:38)

aP2 antisense
5'-AAATTTCCATCCAGGCCTCT-3'       (SEQ ID NO:39)

DLK-1 sense
5'-CTAACCCATGCGAGAACGAT-3'       (SEQ ID NO:40)

DLK-1 antisense
5'-CTTGCACAGACACTCGAAGC-3'       (SEQ ID NO:41)

SMAF1 sense
5'-CTGAGTGTGGCTGTGAGGAG-3'       (SEQ ID NO:42)

SMAF1 antisense
5'-CAGGTCTGACAACGGGAGAT-3'       (SEQ ID NO:43)

ETO sense
5'-CCTGTCAATCCAGACCCAGT-3'       (SEQ ID NO:44)

ETO antisense
5'-TGTCATGGGCTTTCCTCTCTG-3'      (SEQ ID NO:45)

UCP-1 sense
5'-GGCCCTTGTAAACAACAAAATAC-3'    (SEQ ID NO:46)

UCP-1 antisense
5'-GGCAACAAGAGCTGACAGTAAAT-3'    (SEQ ID NO:47)

UCP-3 sense
5'-ACTCCAGCGTCGCCATCAGGATTCT-3'  (SEQ ID NO:48)

UCP-3 antisense
5'-TAAACAGGTGAGACTCCAGCAACTT-3'  (SEQ ID NO:49)

ACRP30 sense
5'-GTTGCAAGCTCTCCTGTTCC-3'       (SEQ ID NO:50)

ACRP30 antisense
5'-TCTCTCCAGGAGTGCCATCT-3'       (SEQ ID NO:51)

AdipoR1 sense
5'-TCTCCTGGCTCTTCCACACT-3'       (SEQ ID NO:52)

AdipoR1 antisense
5'-CCACAATGATGGCAGAGATG-3'       (SEQ ID NO:53)

AdipoR2 sense
5'-TGGAGGCTGTTGGTAGTGAG-3'       (SEQ ID NO:54)

AdipoR2 antisense
5'-TCTTAGGGAACCGAATCACC-3'       (SEQ ID NO:55)

PPARγ sense
5'-GGAATCAGCTCTGTGGACCT-3'       (SEQ ID NO:56)

PPARγ antisense
5'-TGGGTCAGCTCTTGTGAATG-3'       (SEQ ID NO:57)

PPARγ2 sense
5'-CTCCTGTTGACCCACAGCATG-3'      (SEQ ID NO:58)

PPARγ2 antisense
5'-GTGGAGCAGAAATGCTGGAG-3'.      (SEQ ID NO:59)
```

Metabolic Studies

Mice of 9, 16, or 25 weeks old were tested for glucose tolerance (GTT) and those of 18 or 27 weeks old for insulin tolerance (ITT). For GTT, the mice fasted overnight then were injected with glucose intraperitoneally at 1.5 mg/g body weight. For ITT, the mice were given free access to food and injected with insulin intraperitoneally at 0.5 mU/g body weight. The glucose levels were measured in blood withdrawn from the tail vein. To study effects of ASIC3 blockers, salicylic acid (14 mg/kg) or APETx2 (0.23 mg/kg) were injected with glucose or insulin intraperitoneally.

Histology and Morphometric Analysis of Tissues

Periovarian WAT was isolated from each mouse and fixed in the Bouin's solution (Sigma) at room temperature for 24 hours. Then, the fixed tissues were embedded in paraffin, sectioned in 5-μm sections, and stained with haematoxylin and eosin. Morphometric analysis of WAT from 1000 or more cells from 3 to 4 different animals per age group and per genotype involved use of MetaMorph Offline software (Universal Imaging Corporation).

Results

Inhibition of ASIC3 Enhances Insulin Sensitivity that is Age-Dependent

In the present study, it was found that ASIC3−/− mice had a significantly smaller body size than ASIC3+/+ mice and that the ASIC3−/− mice, as they aged, did not build up body fat mass as did ASIC3+/+ mice (n=10-22, p<0.05). The cells of both white and brown adipose tissues in 8-week-old ASIC3−/− mice did not differ in appearance from those of ASIC3+/+ mice. But at 25 weeks, the white adipose tissues of ASIC3−/− mice were full of small adipocytes and some contained multilocular lipid accumulation. In contrast, the brown adipose tissues appeared the same as those of the ASIC3+/+ mice. The mean cell size of adipocytes of 25-week-old ASIC3−/− mice (1018±20 μm$^2$) was much smaller than that of the same-aged ASIC3+/+ mice, as well as 8-week-old mice (1877±39 μm$^2$ in ASIC3+/+ and 1897±41 μm$^2$ in ASIC3−/−).

Because the small adipocytes usually reflect increased insulin sensitivity (Um et al., Nature 431, 200-205, 2004 and Komazawa et al., Nat. Medicine 10, 1208-1215, 2004), experiments were conducted to compare the responses to glucose tolerance test (GTT) and insulin tolerance test (ITT) between the ASIC3−/− and ASIC3+/+ mice (n=6-9 in each group). As the animals aged, the ASIC3−/− mice showed better glucose tolerance and insulin sensitivity than the ASIC3+/+ mice (P<0.05, Mann-Whitney test). In contrast, glucose tolerance and insulin sensitivity in younger mice (from 9 to 18 weeks) did not differ between the 2 genotypes. However, older ASIC3+/+ mice (25 weeks old; n=6) showed significantly poorer results on glucose tolerance test and were more glucose intolerant than younger mice (9 or 16 weeks old; n=6 or 7) (P<0.05). ASIC3+/+ mice of 27 weeks old only had subtle changes in ITT. Such age of ASIC3−/− mice showed no impaired glucose tolerance but, rather improved insulin sensitivity. Put differently, ASIC3−/− mice did not develop age-dependent impaired glucose tolerance (i.e., glucose intolerance). Surprisingly, older ASIC3−/− mice showed better results on the ITT than young mice (n=6, *P<0.05). Compared with ASIC3+/+ mice, ASIC3−/− mice seemed to maintain normal glucose metabolism by improving insulin action with age.

To test whether ASIC3 selective blockers could reverse age-dependent glucose intolerance and insulin resistance, we tested the effects of salicylic acid and APETx2 in the aging mouse groups. Salicylic acid and APETx2 are selective antagonists for ASIC3 in different kinetics (Diochot et al., EMBO J. 23, 1516-1525, 2004 and Voille et al., J. Neurosci. 21, 8026-8033, 2001). It was found that treatment with high dosage salicylic acid could reverse in part the age-dependent effect of glucose tolerance but not affect insulin tolerance test of ASIC3+/+ mice. In contrast, the specific peptide inhibitor of ASIC3, APETx2, could effectively reverse the age-dependent effect of glucose tolerance and significantly enhance the insulin sensitivity in aging ASIC3+/+ mice, as seen on ITT. The differential effects of salicylic acid may be due to the different kinetics in blocking ASIC3 from APETx2 or could be due to an inhibitory effect on IKKβ. Continual treatment with salicylate (120 mg/kg/day) in rodents disrupted IKKβ activity and reversed obesity- and diet-induced insulin resistance by sensitizing insulin signaling.

Age-Dependent Glucose Tolerance is Associated with ASIC3 Expressed in WAT

To examine why the deletion of ASIC3 showed a profound effect in adipocytes, we tested whether ASIC3 is expressed in white adipose tissue (WAT). PCR results revealed the expression of ASIC1b, ASIC3, ASIC4 and ASIC5. In primary WAT culture, we detected the immunoreactivity of ASIC3 in some adipocytes. In young ASIC3+/+ mice (9 weeks old), ASIC3 was evenly expressed in the mature adipocyte fraction and cells of stromal-vascular fraction (SVF) isolated from WAT. Interestingly, WAT-expressed ASIC3 mRNA of the SVF but not mature adipocytes was significantly upregulated (by ~11-fold) in aged mice (30 weeks). In contrast, the expression of ASIC3 in aged dorsal root ganglia (DRG) was only one third of its expression in young DRG.

WAT-Expressed ASIC3 is a Functional Ion Channel

To determine whether WAT-expressed ASIC3 is functional, we applied whole-cell patch recording to examine the acid-evoked currents in cultured SVF cells isolated from mice 8 to 10 weeks old. It was found that acid (pH 5.0) indeed evoked inward currents (sustained or biphasic) in SVF adipose cells. The acid-induced currents were sensitive to selective ASIC3 blockers, salicylic acid and APETx2. 8 adipocytes and 71 stroma-like cells were tested. It was found that acid stimulation elicited an inward current in 5 adipocytes and 40 stroma-like cells. The acid-sensitive adipose cells varied in morphology, cell size (ranging from 15.6 to 64.3 μm in diameter), and kinetics of acid-induced currents. Some of the cells exhibited biphasic currents while others had sustained currents. The electrophysiological properties of the cells with biphasic current differed from those with sustained current in many aspects, including capacitance (35.8 vs 83.7 pF), peak amplitude (314.1 vs 57.6 pA), current density (8.1 vs 2.5 pQ/pF), and rising time (33.6 vs 885.8 ms). The acid evoked biphasic current was found only in stroma-like cells.

No action potential could be induced among these adipose cells, which indicates that they were not contaminated from enteric ganglia or smooth muscle cells. Table 1 below summarizes the cell sizes and electrophysiological properties of adipose cells, comparing cells with sustained currents and cells with biphasic currents. ** $P < 0.01$, t test.

The WAT-expressed ASIC3 was mainly composed of ASIC3 homomeric channels, as indicated by single-cell RT-PCR after whole-cell patch recording. ASIC3-ASIC1b and ASIC3-ASIC2b heteromeric channels were found in a small portion (3/14) of the adipose cells. The acid-sensitive adipose cells also expressed many adipose cell markers, including FAS, FGF10, aP2, ETO, PPARγ, adipoR1, and adipoR2. AdipoR2 was the only marker expressed in all types of cells with acid-induced currents. Surprisingly, 3 cells without acid-evoked inward currents also expressed ASIC3, indicating that the cells may need additional factors to support ASIC3 to form a functional channel. Table 2 below summarizes molecular identity of single-cell RT-PCR in cells with or without acid-evoked inward currents. The adipose cells were sub-grouped according to the expression of ASIC3 homomeric or heteromeric channel. The bracketed numbers indicate cell number that expresses each adipocyte gene marker.

TABLE 2

| Acid-evoked inward current | ASIC gene | Adipocyte markers and other genes | Cell number |
|---|---|---|---|
| Sustained | ASIC3 | CGRP (1), FAS (2), FGF10 (1), aP2 (1), ETO (1), ACRP30 (1), PPARγ (1), AdipoR1 (2), AdipoR2 (3) | 7 |
|  | ASICIb, ASIC3 | aP2 (1), AdipoR2 (1) 2 | 2 |
| Biphasic | ASIC3 | CGRP (1), FAS (1), FGF10 (2), AdipoR1 (1), AdipoR2 (1), PPARγ (1) | 4 |
|  | ASIC2b, ASIC3 | AdipoR2 (1) |  |
| No current | ASIC3 | FAS (1) | 1 |
|  | ASICIb, ASIC3 | FAS (1), FGF10 (1), PPARγ (1), UCP3 (1) | 2 |

The above results indicate that cells in adipose tissue expressed functional ASIC3 channels that may contribute to age-dependent glucose intolerance and insulin resistance. The deletion or inhibition of the channel increased insulin sensitivity in ageing mice. ASIC3-/- mice were smaller in size than ASIC3+/+ mice and accompanied by age related beneficial phenotypes: smaller visceral fat mass, smaller adipocyte size, and better profiles in GTT and ITT. These beneficial phenotypes of ASIC3-/- mice were not due to the diet, as food intake was normal in these mice. In contrast, ageing led to glucose intolerance in ASIC3+/+ mice, which was associated with the upregulation of WAT-expressed ASIC3. ASIC3 signaling in adipose cells but not primary sensory afferents is probably responsible for the age-dependent glucose intolerance because the expression of ASIC3 in dorsal root ganglia declined with age.

ASIC3 is known as the most sensitive acid-sensing ion channel ($pH_{0.5}$ activation ~6.7) and dominantly expressed in

TABLE 1

|  | Diameter (μm) | Vm (mV) | Capacitance (pF) | Peak amplitude (pA) | Current density (pQ/pF) | Rising time (ms) |
|---|---|---|---|---|---|---|
| Sustained (n = 31) | 28.2 ± 2.3 | −18.6 ± 2.3 | 83.7 ± 10.6 | 57.6 ± 10.6 | 2.5 ± 0.4 | 885.8 ± 104.7 |
| Biphasic (n = 14) | 23.8 ± 2.2 | −14.6 ± 2.9 | 35.8 ± 4.4** | 314.1 ± 63.2** | 8.1 ± 2.3** | 33.6 ± 10.1** |
| No current (n = 34) | 24.1 ± 1.6 | −13.6 ± 3.4 | 37.6 ± 3.7 |  |  |  | primary sensory neurons, especially in metaboreceptive sensory neurons or ischemia-sensing neurons. The reasons why the proton sensor ASIC3 mediates signals in adipose tissue may lie in lactate.

Lactic acid produced by anaerobic metabolism is a potent enhancer for acid-sensing ion channels (Immke and MacCleskey, Nat. Neurosci. 4, 869-870, 2001).

Apart from exhausted muscle or ischemic tissues, adipose tissue, especially in old and fat individuals, actively produces lactate as a metabolic product of glucose. Large fat cells from old, fat rodents convert 40% to 50% of the total glucose taken up in lactate as compared with only 5% to 15% in young ones. However, the role of adipose lactate is still ambiguous, because the traditional concept of gluconeogenesis cannot explain how it is actively produced in old, obese subjects. Therefore, lactate may be a signaling compound that coordinates cell and systemic function. Because elevated basal level of lactate is consistently found in diabetic subjects who also display marked insulin resistance, the adipose ASIC3 activity maybe the missing link in the mediation of lactate signaling. ASIC3 responds better to lactic acid than to other acids to depolarize ischemia-sensing neurons. Therefore, these neurons might function as metaboreceptors to sense the anaerobic metabolism of tissues and trigger acid-linked pain sensation in muscle and Heart (Chen et al., 2002). As lactate does not cause pain in many other tissues (e.g., adipose tissues), ASIC3 may function not only as a pain sensor but also in monitoring the metabolic state of tissues. ASIC3 channels open when pH drops from 7.4 to 7.0 and lactate can enhance the opening of ASIC3 at near-physiological pH 7.4 (Immke and McCleskey, Neuron 37, 75-84, 2003). With the ability to detect lactic acidosis, WAT-expressed ASIC3 might be constantly active in adipose tissue of elderly and obese subjects, in whom approximately 50% of total glucose is metabolized to lactate. The tonic signal mediated by WAT-expressed ASIC3 may hamper the glucose uptake by cells and result in the development of insulin resistance with age, when the WAT expression of ASIC3 is also increased. With ASIC3 deficiency, the adipose tissues cannot properly detect lactate and switch the cell fate to enhance insulin sensitivity.

Ageing can result in high levels of circulating lactate and reduce insulin sensitivity. With physiological ageing, resistance to the action of insulin and decline in glucose tolerance develop, resulting in a high prevalence of type 2 diabetes in older people. Type 2 diabetes is the most common metabolic disease in ageing population worldwide and closely associated with mitochondria dysfunction. Because mitochondria dysfunction switches cells to anaerobic glucose metabolism and increases lactate production, it is likely that the lactate sensor, ASIC3, plays a role in control of the age-dependent glucose metabolism.

Human ASIC3 resides within the chromosomal region 7q36 (de Weille et al., FEBS Lett. 433, 257-260, 1998), which was one of the identified quantitative trait loci for fasting glucose, insulin, and insulin resistance (An et al., Diabetes 54, 909-914, 2005). This fact also supports the role of ASIC3.

In sum, the above results suggest that blocking the WAT-expressed ASIC3 signaling is useful in the control of age-dependent insulin resistance and type 2 diabetes.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of identifying a compound for treating insulin resistance, the method comprising:
   contacting a first in vitro cell expressing an acid-sensing ion channel 3 with a test compound, and
   determining an expression or activity level of the acid-sensing ion channel 3 in the cell, and
   identifying the test compound as a candidate compound for treating insulin resistance if the expression or activity level is lower than that determined in the same manner from a second in vitro cell except that the second cell is not contacted with the compound.

2. The method of claim 1, wherein the cell is an adipose tissue cell.

3. The method of claim 2, wherein the adipose cell is a white adipose tissue cell.

4. The method of claim 1, wherein the activity of the acid-sensing ion channel 3 is determined by electrophysical analysis.

5. The method of claim 1, wherein the ion channel activity of the acid-sensing ion channel 3 is determined by whole-cell patch recording, a voltage-sensitive dye, an ion-sensitive dye, or a cytotoxicity assay.

6. The method of claim 1, wherein the method further includes administering the candidate compound to a non-human animal to confirm an efficacy thereof to treat insulin resistance.

7. The method of claim 1, wherein the first cell or second cell is non-neuronal and AdiproR2+.

8. The method of claim 7, wherein the first cell or second cell is selected from the group consisting of NIH3T3 cells, NIH3T3 L1 cells, differentiated NIH3T3 L1 cells, adipose cells, and fibroblast cells.

9. The method of claim 8, wherein the first cell or second cell is positive for one or more of FAS, FGF10, aP2, ETO, PPARγ, and AdipoR1.

10. A method of identifying a compound for treating insulin resistance, the method comprising:

contacting a first cell expressing an acid-sensing ion channel 3 with a test compound, and determining an expression or activity level of the acid-sensing ion channel 3 in the cell, and identifying the test compound as a candidate compound for treating insulin resistance if the expression or activity level is lower than that determined in the same manner from a second cell except that the second cell is not contacted with the compound, wherein the compound is selected from the group consisting of proteins, peptides, peptidomimetics, peptoids, antibodies, small molecule compounds, and drugs.

* * * * *